(12) United States Patent
Steinman et al.

(10) Patent No.: US 9,723,830 B2
(45) Date of Patent: Aug. 8, 2017

(54) FILTRATION IN ORGAN PERFUSION APPARATUS

(71) Applicant: LIFELINE SCIENTIFIC, INC., Itasca, IL (US)

(72) Inventors: Christopher P. Steinman, Sandy, UT (US); Jeffrey S. Louis, Akron, OH (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 0 days.

(21) Appl. No.: 14/739,800

(22) Filed: Jun. 15, 2015

(65) Prior Publication Data

US 2015/0272111 A1 Oct. 1, 2015

Related U.S. Application Data

(62) Division of application No. 13/545,598, filed on Jul. 10, 2012.

(51) Int. Cl.
*A01N 1/02* (2006.01)

(52) U.S. Cl.
CPC .................................. *A01N 1/0247* (2013.01)

(58) Field of Classification Search
CPC .................................................... A01N 1/0247
See application file for complete search history.

(56) References Cited

U.S. PATENT DOCUMENTS

| | | | |
|---|---|---|---|
| 3,701,433 A * | 10/1972 | Krakauer | A61M 1/3627 210/436 |
| 3,995,444 A | 12/1976 | Clark et al. | |
| 4,837,390 A | 6/1989 | Reneau | |
| 4,954,251 A * | 9/1990 | Barnes | B01D 29/23 210/323.2 |
| 5,217,860 A | 6/1993 | Fahy et al. | |
| 5,326,706 A | 7/1994 | Yland et al. | |
| 5,338,662 A | 8/1994 | Sadri | |
| 6,673,594 B1 * | 1/2004 | Owen | A01N 1/02 435/284.1 |
| 7,749,693 B2 | 7/2010 | Brassil et al. | |
| 7,824,848 B2 | 11/2010 | Owen et al. | |

(Continued)

FOREIGN PATENT DOCUMENTS

| | | |
|---|---|---|
| WO | 02/26034 A2 | 4/2002 |
| WO | 2004/089235 A2 | 10/2004 |
| WO | 2011/037512 A1 | 3/2011 |

OTHER PUBLICATIONS

Jan. 13, 2015 International Preliminary Report on Patentability issued in PCT/US2013/049590.

(Continued)

*Primary Examiner* — Nathan Bowers
*Assistant Examiner* — Lydia Edwards
(74) *Attorney, Agent, or Firm* — Oliff PLC

(57) ABSTRACT

A filter for filtering perfusate is integrated with an exterior portion of an organ container. The filter may be used in an apparatus for perfusing an organ. The perfusion apparatus may include an organ container configured to contain an organ, the filter integrated with an exterior portion of the organ container, and another filter. At least the filter integrated with an exterior portion of the organ container may be provided in a sterilized disposable kit.

32 Claims, 5 Drawing Sheets

(56) References Cited

U.S. PATENT DOCUMENTS

| | | |
|---|---|---|
| 2002/0012988 A1 | 1/2002 | Brasile |
| 2002/0177117 A1 | 11/2002 | Wolf |
| 2003/0073227 A1 | 4/2003 | Hull et al. |
| 2004/0058432 A1 | 3/2004 | Owen et al. |
| 2005/0147958 A1 | 7/2005 | Hassanein et al. |
| 2006/0148062 A1* | 7/2006 | Hassanein ................ A01N 1/02 435/284.1 |
| 2007/0026376 A1 | 2/2007 | Lee et al. |
| 2007/0098694 A1 | 5/2007 | Khuri et al. |
| 2011/0076666 A1 | 3/2011 | Brassil |

OTHER PUBLICATIONS

"Precision Woven Synthetic Monofilament Fabrics", by Sefar, obtained Mar. 20, 2012.
"Capsule Filters", by Meissner Filtration Products, Inc., obtained Mar. 20, 2012.
Jul. 8, 2013 Search Report issued in International Application No. PCT/US2013/049590.
Jul. 8, 2013 Written Opinion issued in International Application No. PCT/US2013/049590.
"LifePort Kidney Transporter—Operator's Manual", Organ Recovery Systems, Jul. 21, 2007, pp. 1-47, http://web.archive.org/web/20070721022154/http://www.organ-recovery.com/pdfs/Kidney_Transporer/LifePort_Operators_Manual.pdf.
"LifePort Sterile Disposables", Organ Recovery Systems, May 9, 2009, http://web.archive.org/web/20090509191207/http://www.organ-recovery.com/products.php?id=1.
Nov. 9, 2016 Office Action issued in Chinese Application No. 201380046858.5.

* cited by examiner

FILTRATION IN ORGAN PERFUSION APPARATUS

This application is a divisional application of U.S. patent application Ser. No. 13/545,598, filed on Jul. 10, 2012. The disclosure of the prior application is hereby incorporated herein by reference in its entirety.

BACKGROUND

Related technical fields include organ and tissue perfusion apparatuses that are capable of sustaining and/or restoring viability of organs or tissue and preserving organs or tissue for storage and/or transport, and more particularly that include filters for filtering perfusate.

It is known to perfuse an organ or tissue with a perfusate in order to maintain and sustain the organ or tissue ex vivo. The perfusate usually contains additives and/or nutrients to help maintain the organ or tissue. The perfusate enters into the organ, for example through a blood vessel, and exits the organ through, for example, another blood vessel or other routes. As a result, the perfusate that has passed through the organ or tissue may contain organic matter dispelled from the organ or tissue.

Known perfusion machines may have one or more filters. See, for example, U.S. Pat. No. 7,824,848 to Owen et al.

SUMMARY

In conventional perfusion machines, perfusate is often recirculated and may lead to clogging and contamination of filters. Additionally, a problem with integration filters (filters that stack two filtering mediums directly next to and/or in contact with one another) is that they limit the amount of effective filtration area of the finer filter. Accordingly, the filters may frequently require replacement and also sterilization, along with other parts of the organ perfusion system that come into contact with the perfusate, for their continued function. To replace or resterilize a filter, the sterile environment around the organ or tissue is compromised because the filter is removed from the fluid circuit. Removal of the filter from the fluid circuit causes a break in the fluid circuit and exposes the perfusate in the fluid circuit. As a result, sterility is compromised and the organ or tissue may no longer be free from contamination. This could result in loss of or damage to the organ or tissue.

For example, a relatively large piece of tissue may break free from an organ during perfusion. The piece of tissue may be caught in a filter and/or cover the entire filter, if the piece of tissue is large enough, blocking the fluid circuit and thereby stopping perfusion of the organ. In this scenario, the tubing and/or organ container must be opened to remove the clogged filter and either replace the filter or clean the filter such that perfusate may continue to move in the fluid circuit. However, when the tubing and/or organ container is opened, sterility is compromised because the perfusate and/or the organ itself are exposed to contamination.

A need exists for a perfusion machine that has replaceable or single-use parts, including filter(s), which come into contact with the perfusate fluid. Additionally, a need exists for disposable parts that are easy to replace and that may be easily integrated in the perfusion machine. For example, a need exists for a perfusion machine that has a replaceable organ or tissue container, filter(s), and tubing. It is preferable that the replaceable or single-use parts be sterilized and placed into a saleable package prior to use. Once the container, filter(s), and/or tubing are ready for use, it is desirable that the kit may be opened and the container, filter(s), and tubing may be used with the perfusion machine. Accordingly, there is a need for a kit that allows for the container, filter(s), and tubing to be swapped in and out of a perfusion machine with ease and without worry of comprising the sterility of the perfusion machine. Once an organ or tissue is removed from the perfusion machine, the container, filter(s), and/or tubing may be discarded and replaced without being used for another organ or tissue. Additionally, there is a need for a filter system that has an extended lifetime such that the filters do not need to be replaced during perfusion, transport, and/or storage of an organ or tissue inside the perfusion machine.

Advantages of various embodiments of the present invention include an organ or tissue container and a filter that are integrated together to provide a replaceable unit that improves ease of manufacturing. Additionally, the filter system and container improve the life of the filter system because the filter system is designed to prevent clogging from tissue from the organ or tissue. The container and filter may be sold together as a single unit. The container and filter allow for use together with a single organ or tissue, or multiple organs or tissues, and may preferably be discarded before another organ or tissue is perfused in a perfusion machine. For ease of reference herein, the term "organ" will mean "organ and/or tissue" unless otherwise indicated.

According to exemplary implementations, a filter for filtering perfusate integrated with an exterior portion of an organ container is provided. The filter may be molded monolithically with an exterior portion of the organ container. The filter may alternatively be fastened to an exterior portion of the organ container. For example, the filter may be fitted into an aperture of the organ container. The filter may be disposed within the exterior portion of the organ container. The exterior portion of the container may be located on a bottom or side of the organ container. The exterior portion may be a wall of the organ container. As used herein, the term "wall" includes bottom and/or side walls unless otherwise indicated.

In exemplary implementations, an apparatus for perfusing an organ includes an organ container configured to contain an organ, a first filter integrated with an exterior portion of the organ container, and a second filter. The second filter may be disposed downstream from the first filter. The exterior portion of the organ container may be a side and/or bottom wall of the organ container. The first filter may preferably be a coarser filter than the second filter. The second filter may be disposed within a fluid conduit downstream of the first filter in a perfusate flow path. Further, the fluid conduit may be connected to the first filter. A pump may be disposed between the first filter and the second filter in the perfusate flow path. The first filter may be configured to block particles that would clog the fluid conduit of the perfusate flow path.

In exemplary implementations, the apparatus may include a fluid conduit, a pump, a pressure sensor, an oxygenator membrane, and a combination bubble trap-pressure accumulator to remove bubbles and reduce pulsatility from the pump. The perfusate flow path may, for example, begin at the first filter and then pass, in order, the fluid conduit, the pump, the pressure sensor, the second filter, the oxygenator membrane and the bubble trap before returning to the organ container. Moreover, an organ may be disposed in a perfusate bath inside the organ container. The organ container may be configured to have an exterior surface in contact with a cooling medium. The organ perfusion apparatus may have an organ supporting surface that is one of a plurality of walls of the organ container. The first filter may be integrated with the organ supporting surface. The apparatus may further comprise a cradle disposed within the organ container and having an organ supporting surface configured to support an organ. The cradle may be configured to hold an amount of perfusate to form a perfusate bath around an organ placed inside the cradle.

Implementations may include a sterilized disposable kit comprising an organ container configured to contain an organ and a first filter, configured to filter perfusate, integrated with an exterior portion of the organ container. The kit may also have a second filter. The first filter in the kit may be coarser than the second filter. Additionally, the kit may have an organ supporting surface. The organ supporting surface may or may not be integrated with or part of the exterior portion of the organ container.

In embodiments, a method for perfusing an organ includes filtering perfusate after it leaves the organ with a first filter integrated with an exterior portion of an organ container and filtering the perfusate with a second filter downstream of the first filter. The method for perfusing the organ may utilize a filter for filtering perfusate that is integrated with an exterior portion of an organ container. The filter may, for example, be gravity fed or pump fed. A step of filtering the perfusate fluid with the first filter integrated with the exterior portion of an organ container may be performed before filtering the perfusate fluid with the second filter.

A method of manufacturing an organ container may include forming a filter in an exterior portion of an organ container. The step of forming may include insert molding the filter in an exterior portion of the organ container, which organ container may be injection molded. The method of manufacturing an organ container may include providing a filter material, securing the filter material in an exterior portion of the organ container, and forming a connection on the organ container. The connection may be configured to connect with an organ perfusion apparatus.

Other advantages, benefits and features of the present invention will become apparent to those skilled in the art upon reading the detailed description of embodiments.

DETAILED DESCRIPTION OF EMBODIMENTS

Referring to the accompanying drawings, exemplary embodiments of a perfusion apparatus, filters, and methods according to the invention will be described.

The following description refers to a perfusion apparatus, which may be a transport apparatus, diagnostic apparatus, and/or storage apparatus for an organ or tissue. Although the exemplary systems and methods according to this disclosure may be applicable to specific applications, the depictions and/or descriptions included in this disclosure are not intended to be limited to any specific application. Any perfusion apparatus that may advantageously include an organ or other biological samples as described in an exemplary manner in this disclosure is contemplated.

A filtering apparatus for filtering perfusate may include an organ container configured to connect with an organ perfusion apparatus and having a filter element integrated with an exterior portion of the organ container. An apparatus for perfusing an organ may include an organ container configured to contain an organ, a recirculating perfusate flow path, a first filter integrated with an exterior portion of the organ container in the perfusate flow path, and a second filter in the perfusate flow path. The apparatus may further include a pump, a pressure sensor, an oxygenator, and a bubble trap.

Figure 1:
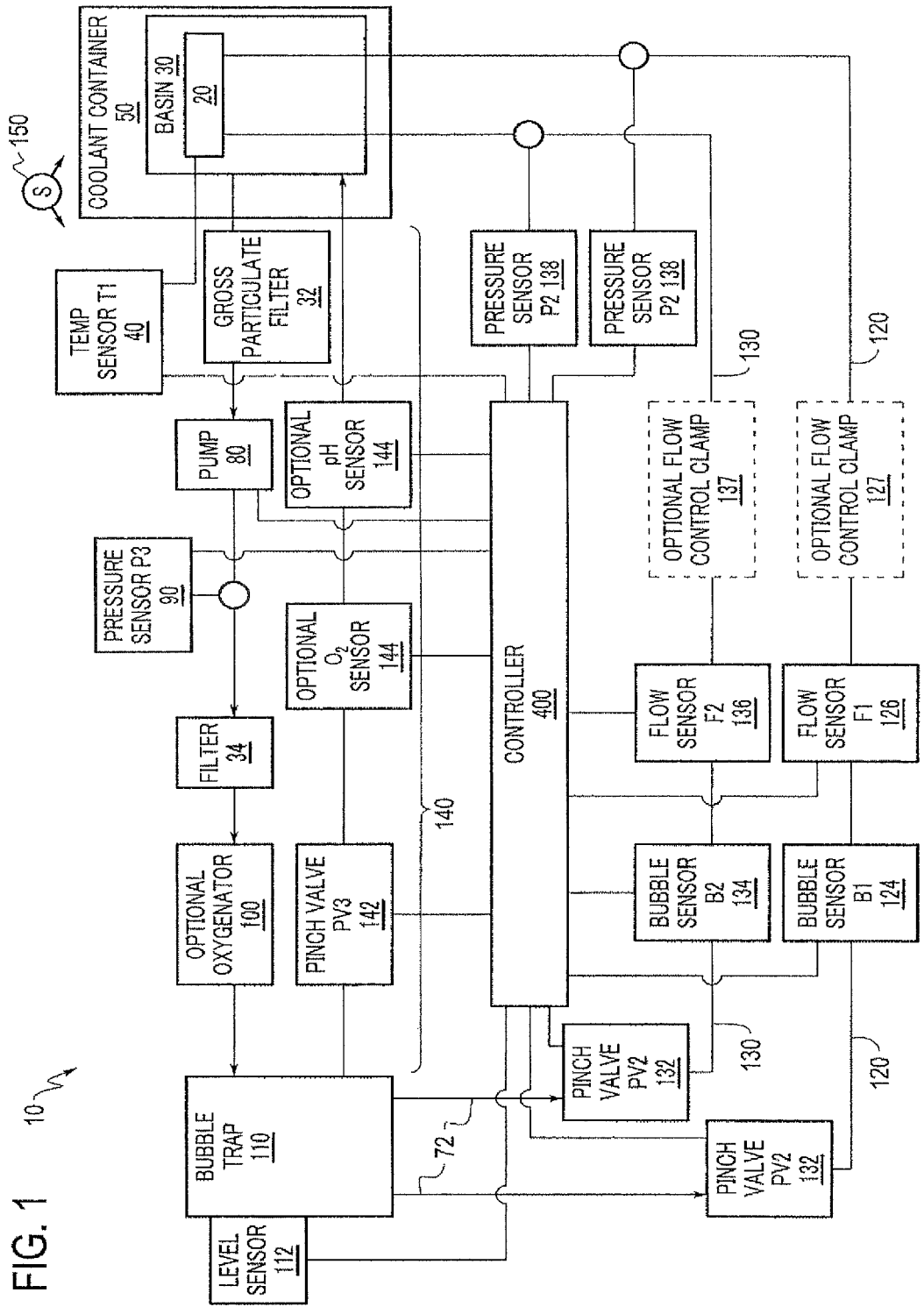
FIG. 1 is a schematic diagram of an exemplary organ perfusion apparatus.
Figure 2:
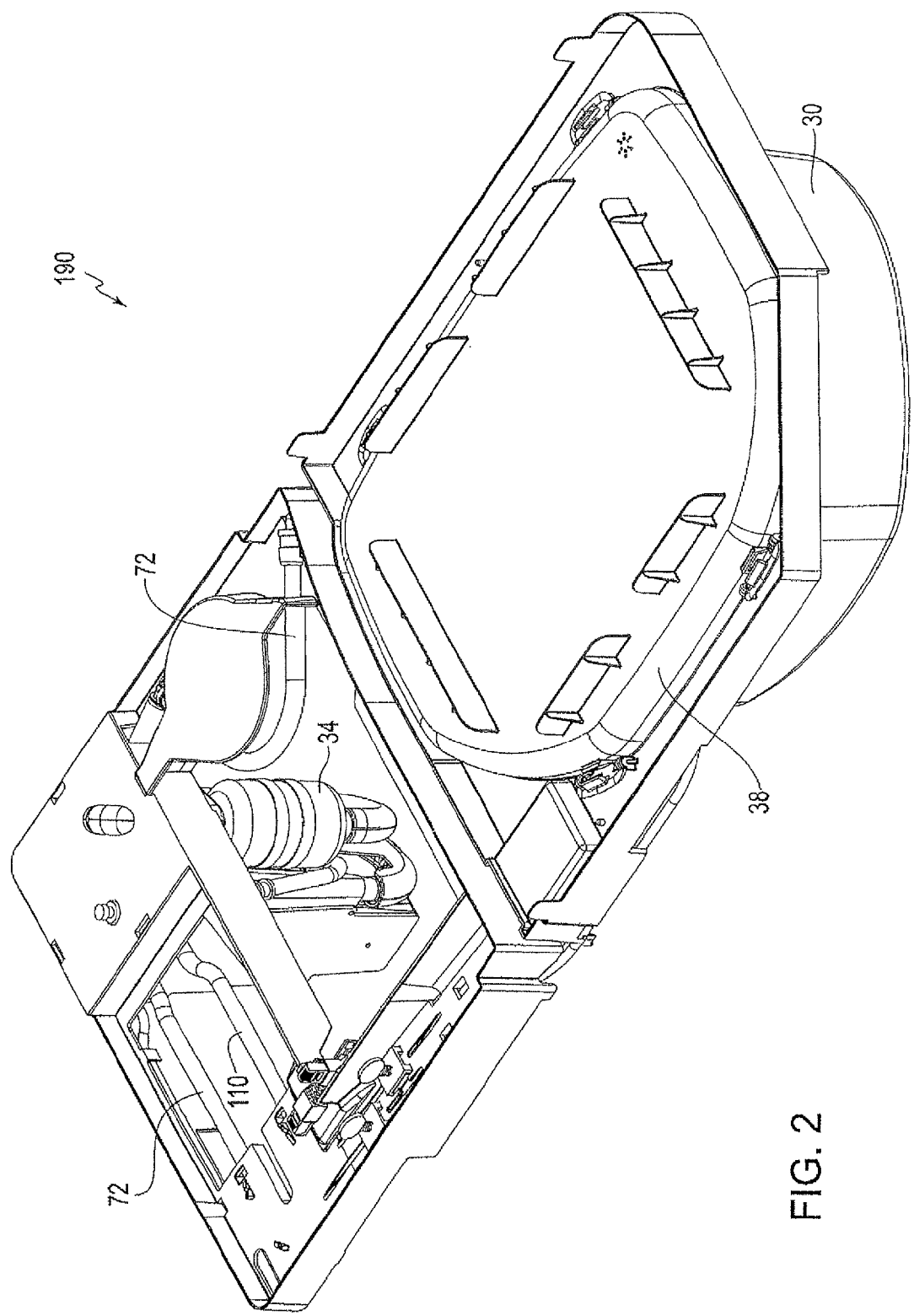
FIG. 2 is a perspective view of an assembly of disposable components of an organ perfusion apparatus.
Figure 5:
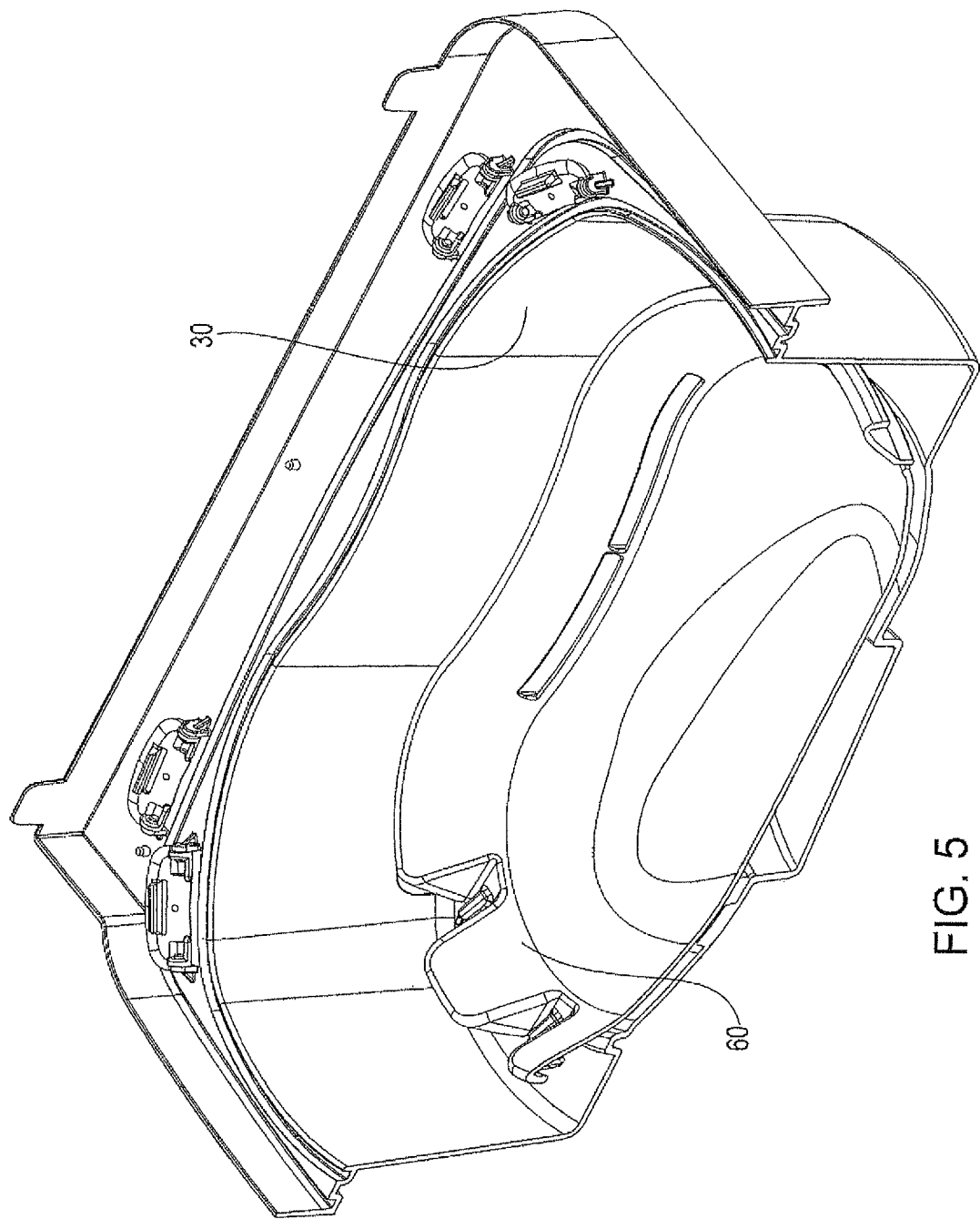
FIG. 5 is a cross-section of a perspective view of a cradle and basin of an organ perfusion apparatus.

FIG. 1 is a schematic diagram of a perfusion apparatus 10 for an organ 20. The organ 20 may preferably be a liver but may be any human or animal, natural or engineered, healthy, injured or diseased organ or tissue. The apparatus includes a basin 30 in which the organ may be placed. As shown in FIG. 2, the basin may have a lid 38 that covers the basin so as to completely enclose the organ 20. The organ 20 may be disposed in a perfusate bath inside the basin 30. In such a configuration, the basin 30 may include an organ supporting surface configured to hold the organ 20 when the organ is in the perfusate bath. Referring back to FIG. 1, the basin 30 may hold a cradle 60 (see FIG. 5), which preferably includes a surface on which the organ 20 is disposed when the organ 20 is in the apparatus 10. The basin 30 may include a first filter 32 (see FIG. 3) that can function as a gross particulate filter. The basin 30 and/or the cradle 60 are preferably configured to allow a perfusate bath to form around the organ 20.

Preferably, the organ 20 may be disposed in a perfusate bath inside of the cradle 60. The cradle 60 may be configured to hold an amount of perfusate to form a perfusate bath around the organ 20 placed inside the cradle 60. The perfusate bath may partially immerse the organ 20 or may fully immerse the organ 60. The cradle 60 and basin 30 may be designed such that overflow from the perfusate bath in the cradle 60 is received inside of the basin 30, which may form a secondary bath.

The perfusate bath preferably collects in the basin 30 before it passes through the first filter 32. The perfusate flows through the first filter 32, such as by gravity or by way of pump 80. When the perfusate is gravity fed through the first filter 32, the first filter 32 may be typically located at or near a bottom portion of the basin 30 such that gravity pushes the perfusate through the first filter 32. However, the pump 80 may apply a pressure or negative pressure (suction) to the perfusate such that the perfusate passes through the first filter 32. The pump 30 may be used in configurations in which the first filter 32 is not located at or near a bottom portion of the basin 30.

The basin 30 may also include a temperature sensor 40 located in or near the cradle 60. The basin may include multiple temperature sensors 40, which may provide redundancy in the event of a failure and/or may provide temperature measurement at multiple locations. Preferably, the temperature sensor 40 is an infrared temperature sensor. The temperature sensor 40 is preferably disposed as close as practical to the organ 20 when the organ 20 is disposed in the cradle 60 in order to improve the usefulness and accuracy of the temperature sensor 40, which preferably provides a temperature measurement of the perfusate that may be correlated to a temperature of the organ 20. Alternatively or additionally, the temperature sensor 40 may be used to directly measure the temperature of the organ 20.

The basin 30 is preferably disposed within an insulating cooling container 50 that may contain cold materials such as ice, ice water, brine or the like, or may be cooled by a cooling device such as an electrical or gas powered cooling device. Cooling container 50 may be permanently or removably attached to, or an integral, monolithic part of, apparatus 10. Thus, in use as shown in the Figures, the organ 20 is disposed within the cradle 60, which is disposed within the basin 30, which is disposed within the cooling container 50. Preferably, each of the basin 30, cradle 60 and cooling container 50 is configured, or keyed, to fit within its corresponding mating component in a single orientation. The configuration of the cooling container 50, basin 30 and cradle 60 may provide a configuration that provides cooling for the organ 20 without the contents of cooling container 50 contacting the organ 20 or the cradle 60. The basin 30 may be configured to have an exterior surface in contact with a surface of the cooling container 50, which provides thermal communication with a cooling medium in the cooling container 50. Although the cooling container 50 is described herein as containing ice, any suitable cooling medium can be used. Ice may be preferable due to the ease with which ice can be procured, but one of ordinary skill would understand that any suitable cooling medium, which could be an active cooling medium (such as a thermo electric cooler or a refrigerant loop) or a passive cooling medium similar to ice or ice water, or a combination thereof, may be utilized. The amount of ice, or other cooling medium, that can be placed within the cooling container 50 may, for example, be determined based upon the maximum time that cooling is likely to be provided while the organ 20 will be in the apparatus 10.

The cradle 60 may include components configured to securely restrain the organ 20 in place. Such components may, for example, include user selectable netting that is fastened to the cradle 60. The cradle 60 may also have an organ supporting surface configured to support the organ 20. The organ supporting surface may be a surface that is shaped to receive the organ 20 in a shape that is complementary to the general shape of the organ in a preferred orientation of the organ.

FIG. 2 is a perspective view of an exemplary arrangement of disposable components 190 of the organ perfusion apparatus 10. The disposable components 190 preferably include the basin 30, which may be configured to contain an organ 20. The first filter 32 may be integrated with an exterior portion of the basin 30 and a second filter 34 may also be provided. The second filter 34 may be disposed downstream from the first filter in a fluid conduit 72 that defines a first flow path 70. The fluid conduit 72 may be connected to the first filter 32 and/or may be connected to an exterior or interior portion of the basin 30. Preferably, all components of the apparatus 10 that come into contact with perfusate and/or the organ 20 are disposable and/or easily replaced, most preferably as a single unit with most or all parts connected together as shown in FIG. 2. The components of the organ perfusion apparatus that are not disposable may be reused indefinitely.

The disposable components 190 of the organ perfusion apparatus 10 may preferably be sterilized prior to use. Some or all of the disposable components 190 may be provided in the form of a sterilized disposable kit. For example, the sterilized disposable kit may comprise the basin 30, the first filter 32, and the second filter 34. The sterilized disposable kit may further include the organ supporting surface, and/or other parts of the disposable components 190 such as the conduits, oxygenator membrane, and bubble trap. The disposable components 190 are preferably manufactured in a clean environment and sterilized as a completed saleable unit with seal packing functioning as a sterile barrier. The packing protects the sterilized, disposable components from being contaminated. The disposable components 190 may be sterilized while in the package. Once the components 190 are ready for use, the package may be opened and the components 190 may be used with the organ perfusion apparatus 10. This allows the sterilized, disposable components to be "single-use" components. That is, once an organ 20 is removed from the basin 70, the sterilized, disposable components 190 may be discarded and replaced without being used for another organ. Accordingly, the organ perfusion apparatus 10 maintains strict sterility and prevents contamination of an organ 20 being perfused, transported, and/or stored in the organ perfusion apparatus 10.

Such a kit may include packaging such as plastic or shrink wrap packaging containing some or all of the components that come into contact with an organ 20 and/or perfusate. In embodiments, the tubing, filter, oxygenator and bubble trap are packaged together, and the cradle and basin are packaged individually or together, and optionally together with the tubing, filter, oxygenator and bubble trap in a manner preconfigured to be placed into a flow path arrangement of fixed-location parts in apparatus 10, for example as shown in FIG. 2.

After passing through the filter 32, the perfusate flows along a first flow path 70 that includes a suitable fluid conduit 72, such as flexible or rigid tubing, passing a pump 80, a pressure sensor 90, a second filter 34, an oxygenator 100, and a bubble trap 110, each of which is discussed below. The second filter 34 may be gravity fed or pump fed similar to the first filter 32.

The first filter 32 is preferably a coarser filter than the second filter 34 such that the first filter 32 preferably blocks relatively larger particles and the second filter 34 preferably blocks relatively smaller particles. Accordingly, the mesh, membrane, or other structure or material used for the first and second filters 32, 34 may be different and finer in the second filter 34 than in the first filter 32. In some embodiments, the first filter 32 can be configured to filter certain types of organ matter while the second filter 34 is configured to filter different types of organ matter. The first filter 32 may be a relatively large filter compared to the second filter 34. The first filter 32 preferably provides filtration that is fine enough to at least block particles that would clog the fluid conduit 72 of the perfusate flow path 70 (e.g., particles that are larger than an interior diameter of the flow path) while the first filter 32 itself does not become clogged. Finer filtration may also be provided in the first filter.

For example, the first filter 32 may be a screen filter and the second filter 34 may be a cartridge or capsule filter. The first filter 32 may preferably be made of a monofilament fabric and may be made of a polymer, metallic, or composite material. The first filter 32 may be any shape, including cylindrical or pleated, or a non-woven depth filter, preferably round and flat, or insert molded or potted, and have a diameter between 0.1 to 20 inches, preferably between 1 to 10 inches, and most preferably between 4 to 5 inches. The first filter may have an average opening size of 10 to 10,000 microns and preferably 100 to 3,000 microns. Such a coarse filter may be provided to prevent large particles, which may include byproducts of the organ or of the organ being removed from the donor, from entering and clogging fluid paths of the apparatus 10.

The apparatus 10 may include upstream tubing and peristaltic pump segment tubing that may be any diameter. For example, upstream tubing that is located between the first filter 32 and the bubble trap 110 may be nominally between 0.03 to 1 inch inner diameter, preferably 0.1 to 0.5 inches inner diameter, and more preferably between 0.35 to 0.4 inches inner diameter. For example, the upstream tubing may be about 0.375 inches in inner diameter with a cross sectional area of 0.110 square inch. The upstream tubing is preferably clear, with a controlled wall thickness and controlled stiffness (durometer) preferably about Shore-A-40. This tubing may preferably be PVC but can be made of any TPE or thermoplastic, medical grade material. For example, peristaltic pump segment tubing may be nominally between 0.01 to 1 inch inner diameter, preferably 0.1 to 0.5 inches inner diameter, and more preferably 0.3 to 0.325 inches inner diameter. For example, the peristaltic pump segment tubing may be about 0.312 in inner diameter and is a thermoplastic set such as silicone but can be any other plastic material such as PVC or a TPE. This material is also a controlled durometer and wall thickness. With a 4.5 inch diameter filter having a cross sectional surface area of 15.9 square inches, the ratio of cross sectional areas between the first filter 32 and the upstream tubing is 144:1. However, the ratio of cross sectional area between the first filter 32 and the upstream tubing may be any ratio such that the first filter 32 prevents pieces of tissue from clogging the upstream tubing.

The first filter 32 may be an integral part of the basin 30 or the first filter may be disposed elsewhere in the first flow path 70 downstream of the basin 30. The first filter 32 may also be a separate component disposed on, inside or outside of the basin 30 or disposed within the fluid conduit 72.

The second filter 34 may be any filter capable of filtering perfusate. For example, the second filter 34 may be a compact, pleated filter element that is integrally sealed into a housing. The housing may be, for example, polypropylene or any other suitable polymer or composite material. The filter element and housing may be thermally bonded into a self-contained unit to form a cartridge and capsule. The second filter 34 may preferably have a filter surface area of 0.25 ft$^2$ to 0.75$^2$ and more preferably about 0.45 ft$^2$ to 0.55 ft$^2$, such as 0.5 ft$^2$.

The first filter 32 may be made integral with the basin 30 in numerous ways. For example, the first filter 32 may be molded into or as part of a molded basin 30. Examples of molding techniques include injection molding, cast molding, compression molding, and other molding techniques appreciated by one skilled in the art. The basin 30 may be molded around the first filter 32 such that the basin 30 is integrated with the first filter 32 around a perimeter edge or circumference of the first filter 32. The first filter 32 may be placed in a mold cavity or die and subsequently have a resin, polymer, or metallic material formed around the first filter 32 such that the first filter 32 is connected to the basin 30. The first filter 32 may alternatively be inserted and held in place with a separate, molded, retaining feature such as a simple ring or snap ring. The first filter 32 may also be fastened to the basin 30 in other ways. For example, the first filter 32 may be fastened by threaded (such as screws, nuts and bolts) or non-threaded fasteners, adhesives, hook-and-loop fasteners, or other fastening techniques appreciated by one skilled in the art. Moreover, the first filter 32 may be fitted into an aperture of the basin 30. The first filter 32 may be dimensioned such that the aperture within the basin is slightly larger, exactly the same size, or slightly smaller than the dimensions of the first filter 32. The first filter 32 may then be pushed and/or placed inside the aperture with enough force to fit the first filter 32 securely within the basin 30. The first filter 32 may, for example, be press-fitted, snap-fitted, or screwed into the aperture of the basin 30. Additional ways of securing the first filter 32 into the basin may employ hooks, tabs, covers, and/or other securing devices appreciated by those skilled in the art. The first filter 32 may also be disposed inside of an exterior portion of the basin 30. For example, the first filter 32 may be disposed inside a wall of the basin 30 such that the outer circumference or periphery of the first filter 32 is between two surfaces of the wall (as shown in FIG. 3).

The exterior portion of the basin 30 may be a wall of the basin or may be another structure attached to the basin 30 or a part of the basin 30. For example, the exterior portion may be a structure configured specifically to hold the first filter 32. The first filter 32 may be detachable from the basin 30 or may be permanently integrated with the basin 30. The exterior portion may also be other structure that has an exterior surface facing an outside of the basin 30. The exterior portion of the basin 30 may be located on a bottom of the basin 30. The exterior portion of the basin 30 may be the bottommost structure of the basin 30 and/or it may be an intermediate structure of the basin 30. The exterior portion may be a wall of the basin 30. Additionally, as discussed above, the basin 30 may have an organ supporting surface upon which the organ 20 is placed and this organ supporting surface may be an inner surface of the basin with which the first filter is integrated.

Figure 3:
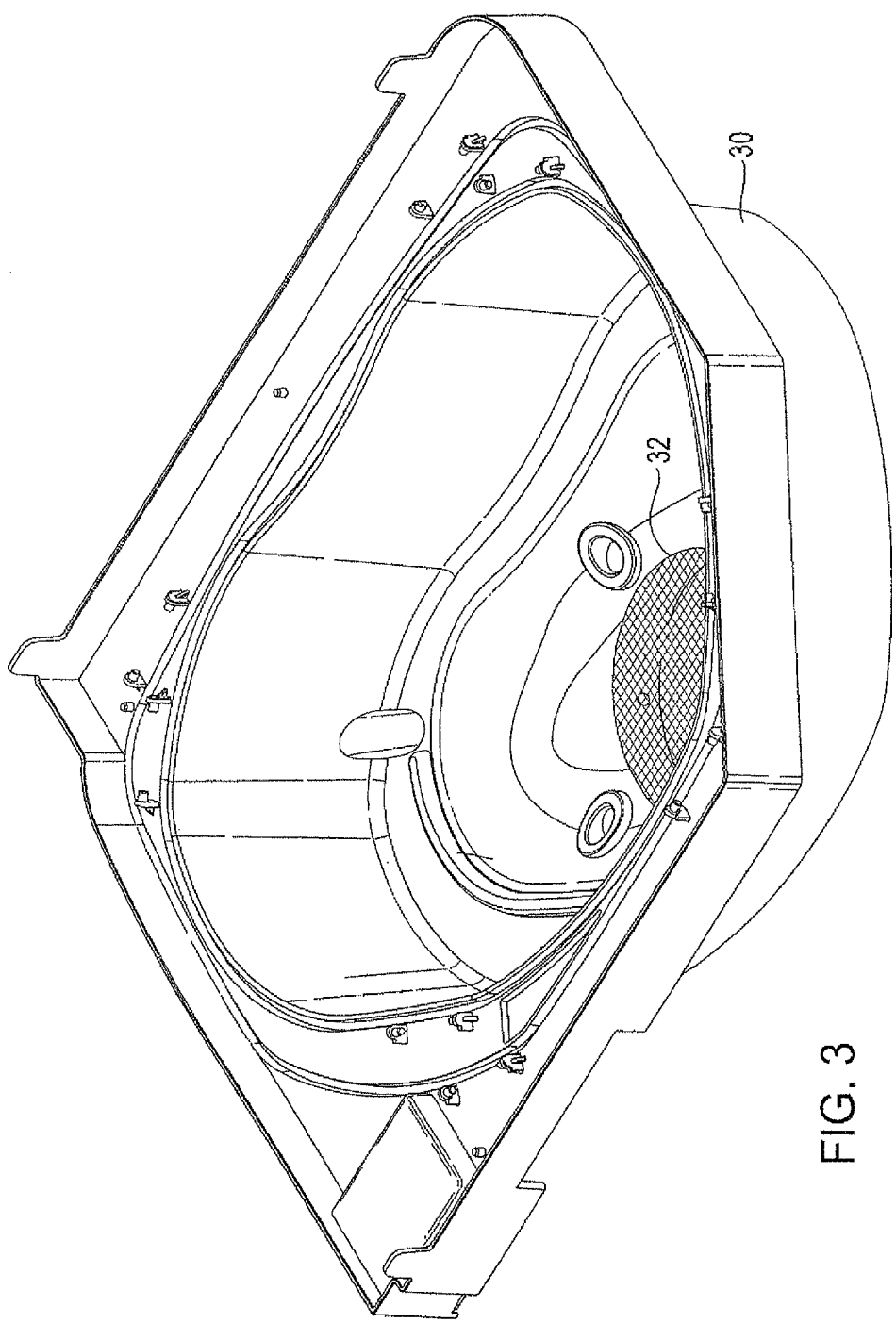
FIG. 3 is a view of a filter integrated with a basin of an organ perfusion apparatus.
Figure 4:
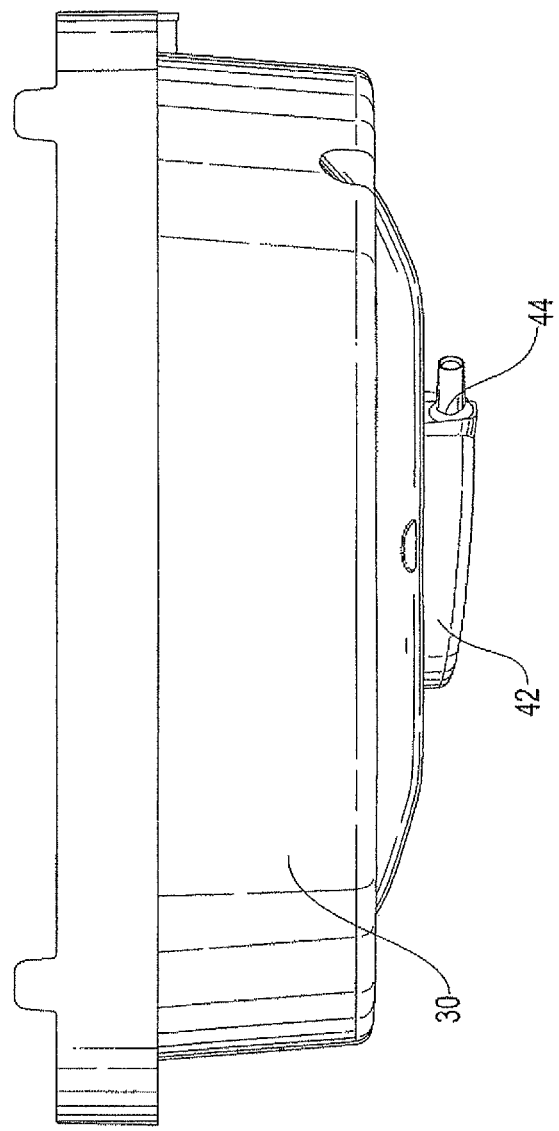
FIG. 4 is a side view of a basin of an organ perfusion apparatus.

FIG. 3 shows an example of the first filter 32 integrated with an exterior portion of the basin 30. FIG. 4 shows an extended portion 42 of the basin 30. As illustrated, the extended portion 42 generally has a cylindrical or other shape and is located on a bottom of the basin 30. The extended portion 42 may be in the shape of a cup on the bottom of the basin 30. The extended portion 42 may have an end surface that is angled (e.g., substantially perpendicular) relative to the length of the extended portion 42. The end surface may be partially or completely angled such that all or part of the end surface of the extended portion 42 is not perpendicular to a side wall of the extended portion 42. One side of the extended portion 42 may be open and the other end of the extended portion 42 may be closed or sealed. The extended portion 42 may be located in a substantially center area or at a side of a bottom of the basin 30. A width or diameter of the extended portion 42 may preferably be larger than the height or length of the extended portion 42. The extended portion 42 may be integral with the basin 30 and may be molded monolithically with or attached to the basin. The extended portion 42 may define a secondary chamber between the first filter 32 and the fluid conduit 72. Various manufacturing techniques may be used to form the extended portion 42 of the basin 30. The extended portion 42 preferably has a port 44 that is connected to the fluid conduit 72 (not shown in FIG. 4). This configuration and structure of the first filter 32 and basin 30 may allow for organ matter that is larger than a diameter of the fluid conduit 72 to be filtered out by the first filter 32 without clogging the first filter 32 due to the diameter of the first filter being relatively larger than the diameter of the fluid conduit 72.

The first flow path 70 may also include a pump 80. The pump 80 may be any pump that is suitable in connection with perfusing of organs. Examples of suitable pumps may include hand operated pumps, centrifugal pumps and roller pumps. If a roller pump is included, the roller pump may include a single channel or flow path (where only one tube is compressed by the rollers) or the roller pump may include multiple channels or flow paths (where multiple tubes are compressed by the rollers). If multiple, parallel channels or flow paths are included, the rollers may preferably be disposed out of phase or offset so that pulses created by the rollers are out of phase, which may result in a fluid flow out of the roller pump that is relatively less pulsatile than would be the case with a single roller. Such a multiple channel roller pump may achieve a constant flow rate or a minimally pulsatile flow rate, which may be advantageous depending on the other components in the flow path and/or the type of organ being perfused. The pump 80 is shown as being disposed between the first filter 32 and the second filter 34, but may be disposed anywhere along the flow path. For example, the pump 80 may be disposed downstream of both the first filter 32 and the second filter 34.

The flow path 70 may include a pressure sensor 90. The pressure sensor 90 may preferably be disposed after the outlet of the pump 80 in order to be used to monitor and/or control the pressure produced at the outlet of the pump by way of a suitable controller, such as a computer, microprocessor, central processing unit, and/or workstation. The pressure sensor 90 may provide continuous or periodic monitoring of pressure.

The flow path 70 may include an oxygenator 100 such as an oxygenator membrane or body to provide oxygenation to the perfusate. Oxygen may be provided to the oxygenator 100 by any suitable means. Suitable oxygen sources may provide pure oxygen or mixed gases such as air. The gas may be compressed, such as in a high-pressure cylinder, liquefied as would be stored in a dewar, or drawn from the surrounding atmosphere. Preferably, the oxygen may be provided by way of an oxygen generator, which may be separate from the apparatus 10 or integral to the apparatus 10. Oxygen may be generated through any suitable means, some examples of which include through pressure swing adsorption using a molecular sieve, through a ceramic oxygen generator (a solid state oxygen pump) or through decomposition of water.

The flow path 70 may include a bubble trap 110. The bubble trap 110 preferably separates gas bubbles that may be entrained in the perfusate flow and prevents such bubbles from continuing downstream and entering the organ 20. The bubble trap 110 may also function as an accumulator that reduces or eliminates pulsatility of the perfusate flow. The bubble trap 110 may include a volume of gas, initially or through the accumulation of bubbles, such that pressure fluctuations in the perfusate are dampened or eliminated.

The bubble trap 110 may include a vent that allows purging of gas during start up or a purging process. The vent may be connected to or part of purge flow path 140 (which is discussed in detail below). The vent is preferably open during a start up process so that any air or other gas may be purged from the perfusate path 70. Once the gas is purged from the perfusate path 70, the vent may preferably be closed. The vent may be closed manually or may be closed automatically by way of a suitable controller.

The bubble trap 110 may include a level sensor 112 to ensure that at least a predetermined air space above the fluid level is maintained. The level sensor 112 may, for example, include a float that includes a magnet that interacts with Hall Effect sensors in the transporter. A level sensor 112 may optionally be used during the purging process to determine when the purging is complete and/or may be used to determine when the purging process needs to be repeated, which may happen after bubbles have been trapped in the bubble trap 110. Also, through use of the level sensor 112 and the vent, the accumulator function of the bubble trap can be tuned to account for differing amplitudes and frequencies of pulsatility in the perfusate flow.

The bubble trap 110 may have any number of outlets, as needed for a given application of the perfusion apparatus. In FIG. 1, three outlets are shown connected to three different flow paths, which may be particularly suited for perfusion of a liver. When perfusing a liver, the three paths preferably include portal flow path 120 connected to the portal vein of a liver, hepatic flow path 130 connected to the hepatic artery of a liver, and bypass flow path 140 that provides a return path to the basin 30.

As shown in FIG. 1, the portal flow path 120 and hepatic flow path 130 may optionally include similar or different components such as valves 122, 132; bubble sensors 124, 134; flow sensors 126, 136; flow control clamps 127, 137; and pressure sensors 128, 138. Each similar component may function in a similar manner, and such pairs of components may optionally be structurally and/or functionally identical to reduce manufacturing costs.

Valves 122, 132 may be pinch valves that function to squeeze tubing and reduce or shut off flow, but any suitable valve may be used. Pinch valves may be advantageous because in normal usage they do not come into contact with the perfusate and therefore do not require replacement and/or cleaning after use.

Preferably, the bubble sensors 124, 134 are ultrasonic sensors disposed around tubing, although any suitable sensor may be used. Similar to pinch valves, ultrasonic sensors may be advantageous because in normal usage they do not come into contact with the perfusate and therefore do not require replacement and/or cleaning after use. Instead, ultrasonic sensors can be disposed in contact with, adjacent to or around an external surface of tubing in order to sense bubbles.

Flow control clamps 127, 137 are optional and may be used to fine-tune the flow rate in one or both of portal flow path 120 and hepatic flow path 130. Preferably, the organ provides self-regulation to control an amount of flow that exits the bubble trap 110 and is divided between the portal flow path 120 and the hepatic flow path 130. In such self regulated flow, pressure sensors 128, 138 provide overpressure monitoring. In the event that pressure delivered to the organ in either or both of the portal flow path 120 or the hepatic flow path 130 exceeds a predetermined threshold, the apparatus 10 can automatically stop and/or reduce the flow rate provided by the pump 80 to prevent damage to the organ. In addition or alternatively, the pressure sensors 128, 138 may be used to generate warning signals to the user and/or to an appropriate controller as pressures approach the predetermined threshold.

After exiting one or both of the portal flow path 120 and hepatic flow path 130, perfusate flows through the organ and returns to the basin 30 to form an organ bath.

Bypass flow path 140 may include a valve 142, and/or sensors such as oxygen sensor 144 and pH sensor 146. Preferably, the valve 142 is a pinch valve and may be of similar configuration to valves 122 and 132, but any suitable valve may be used. The oxygen sensor 144 and the pH sensor 146 may be used to determine the state of the perfusate. Preferably, the bypass flow path 146 is only used during a purging or priming process, although it may also be used during perfusion, preferably continuously, to monitor perfusate properties in real time.

The organ perfusion apparatus 10 may also include an accelerometer 150. Preferably the accelerometer 150 is a three-axis accelerometer, although multiple single axis accelerometers may be used to the same effect. The accelerometer 150 may be used to continuously or periodically monitor and/or record the state of the apparatus 10. Monitoring may include monitoring for excessive shocks as well as attitude (e.g., pitch and yaw) of the apparatus 10. By implementing such monitoring, misuse or potentially inappropriate conditions of the apparatus 10 can be detected and recorded.

The apparatus 10 may include storage compartments for items other than the organ 20. For example, the apparatus 10 may include a document compartment 160 to store documents and/or charts related to the organ 20. Also, the apparatus 10 may include one or more sample compartment 170. The sample compartment 170 may be configured, for example, to store fluid and/or tissue samples. The sample compartment 170 may be advantageously disposed near the cooling container 50 to provide cooling, which may be similar or equivalent to the cooling provided for the organ 20.

The apparatus 10 may include one or more tamper evident closures 180. A tamper evident closure 180 may be used to alert a user that the apparatus 10 has been opened at an unauthorized time and/or location and/or by an unauthorized person. Evidence of tampering may alert the user to perform additional testing, screening, or the like before using the organ 20 and/or the apparatus 10.

What has been described and illustrated herein are preferred embodiments of the invention along with some variations. The descriptions and figures used herein are set forth by way of illustration only and are not meant as limitations. Those skilled in the art will recognize that many variations are possible within the spirit and scope of the invention.

What is claimed is:

1. An apparatus for filtering perfusate, configured to be moved relative to an organ perfusion apparatus, and comprising:
    an organ container having a basin configured to receive an organ or tissue and a perfusate bath, a bottom of the basin having formed therein an opening through which perfusate may flow from the organ container to the organ perfusion apparatus during perfusion of the organ or tissue locatable in the basin; and
    a coarse filter covering the opening at the bottom of the basin so as to be configured to filter any of the perfusate that flows through the opening by preventing large particles in the perfusate from entering the opening, while ensuring a sufficient flow rate of the perfusate through the opening to maintain the perfusion of the organ or tissue,
    wherein the coarse filter is located so that, during the perfusion of the organ or tissue, the coarse filter is accessible to a practitioner by way of another opening in the organ container.

2. The filtering apparatus of claim 1, wherein the coarse filter constitutes an exterior portion of the organ container, the exterior portion at least partly forming the basin.

3. The filtering apparatus of claim 2, wherein the coarse filter is fitted into the opening at the bottom of the basin.

4. The filtering apparatus of claim 2, wherein the coarse filter is disposed in the exterior portion of the organ container such that an outer circumference or periphery of the coarse filter is between two surfaces of the exterior portion of the organ container.

5. The filtering apparatus of claim 1, wherein the coarse filter is detachable from the organ container.

6. The filtering apparatus of claim 1, wherein the coarse filter is a screen filter.

7. The filtering apparatus of claim 1, wherein the coarse filter has an average opening size of 100 microns to 10,000 microns.

8. The filtering apparatus of claim 7, wherein the coarse filter has an average opening size of 1,000 microns to 3,000 microns.

9. The filtering apparatus of claim 7, wherein the large particles are byproducts of the organ or tissue.

10. The filtering apparatus of claim 1, wherein (i) an organ-supporting surface configured to support the organ or tissue and (ii) the opening are on opposite sides of the coarse filter.

11. An apparatus, configured to be moved relative to an organ perfusion apparatus, and comprising:
    an organ container having a basin configured to receive an organ or tissue and a perfusate bath, a bottom of the basin having formed therein an opening through which perfusate may flow from the organ container to the organ perfusion apparatus during perfusion of an organ or tissue locatable in the organ container;
    a recirculating perfusate flow path;
    a coarse filter that is in the perfusate flow path and that covers the opening at the bottom of the basin so as to be configured to filter any of the perfusate that flows through the opening by preventing large particles in the perfusate from entering the opening, while ensuring a sufficient flow rate of the perfusate through the opening to maintain the perfusion of the organ or tissue; and
    a fine filter, less coarse than the coarse filter, downstream of the coarse filter in the perfusate flow path,
    wherein the coarse filter is located so that, during the perfusion of the organ or tissue, the coarse filter is accessible to a practitioner by way of another opening in the organ container.

12. The apparatus of claim 11, wherein the coarse filter constitutes an exterior portion of the organ container, the exterior portion at least partly forming the basin.

13. The apparatus of claim 12, further comprising a cradle disposed within the basin, the cradle having an organ supporting surface configured to support the organ.

14. The apparatus of claim 11, wherein the fine filter is disposed within a fluid conduit that is downstream of the coarse filter and that is in fluid communication with the coarse filter.

15. The apparatus of claim 14, wherein the coarse filter is larger than the fine filter.

16. The apparatus of claim 11, further comprising:
    a pump disposed between the coarse filter and the fine filter in the perfusate flow path.

17. The apparatus of claim 11, wherein the coarse filter is sized to (i) block the large particles that would clog the fine filter while (ii) not becoming clogged itself by the large particles.

18. The apparatus of claim 11, further comprising:
    a pump;
    a pressure sensor;
    an oxygenator; and
    a bubble trap.

19. The apparatus of claim 18, wherein the perfusate flow path comprises a conduit that begins at the coarse filter and then passes, in order, the pump, the pressure sensor, the fine filter, the oxygenator, and the bubble trap before returning to the organ container.

20. The apparatus of claim 11, wherein a width of the coarse filter is between about 4 and 5 inches.

21. The apparatus of claim 14, wherein the coarse filter has an area that is at least two times a cross-sectional area of the fluid conduit.

22. The apparatus of claim 11, wherein the organ container comprises an extended portion that is at a bottom region of the organ container and that forms a secondary chamber between the coarse filter and a fluid conduit.

23. The apparatus of claim 11, wherein the coarse filter is a screen filter.

24. The apparatus of claim 11, wherein the fine filter is a cartridge or capsule filter.

25. The apparatus of claim 11, wherein a filter surface area of the fine filter is about 0.5 ft$^2$.

26. The apparatus of claim 11, wherein the coarse filter has an average mesh opening size of 100 to 10,000 microns.

27. A sterilized disposable kit, configured to be moved relative to an organ perfusion apparatus, and comprising sterilized packaging containing:
- a sterilized organ container having a basin configured to receive an organ or tissue and a perfusate bath, a bottom of the basin having formed therein an opening through which perfusate may flow from the organ container to the organ perfusion apparatus during perfusion of the organ or tissue locatable in the basin,
- a sterilized coarse filter that covers the opening at the bottom of the basin so as to be configured to filter any of the perfusate that flows through the opening by preventing large particles in the perfusate from entering the opening, while ensuring a sufficient flow rate of the perfusate through the opening to maintain the perfusion of the organ or tissue,
- wherein the coarse filter is located so that, during the perfusion of the organ or tissue, the coarse filter is accessible to a practitioner by way of another opening in the organ container.

28. The kit of claim 27, further comprising a sterilized fine filter disposed inside of the sterilized packaging, the coarse filter being coarser than the fine filter.

29. The kit of claim 28, wherein the coarse filter constitutes an exterior portion of the sterilized organ container, the exterior portion at least partly forming the basin.

30. The kit of claim 29, further comprising a fluid conduit, an oxygenator, and a bubble trap, contained in the sterilized packaging.

31. An apparatus for filtering perfusate, configured to be moved relative to an organ perfusion apparatus, and comprising:
- an organ container having a basin configured to receive an organ or tissue and a perfusate bath, a bottom of the basin having formed therein an opening through which perfusate may flow from the organ container to the organ perfusion apparatus during perfusion of the organ or tissue locatable in the basin; and
- a coarse filter covering the opening at the bottom of the basin so as to be configured to filter any of the perfusate that flows through the opening by preventing large particles in the perfusate from entering the opening, while ensuring a sufficient flow rate of the perfusate through the opening to maintain the perfusion of the organ or tissue,
- wherein the coarse filter is located so that, during the perfusion of the organ or tissue, the coarse filter is accessible to a practitioner by way of another opening in the organ container, and
- wherein the coarse filter is disposed inside a wall of the basin that is at least partly formed by an exterior portion of the organ container.

32. An apparatus for filtering perfusate, configured to be moved relative to an organ perfusion apparatus, and comprising:
- an organ container having a basin configured to receive an organ or tissue and a perfusate bath, a bottom of the basin having formed therein an opening through which perfusate may flow from the organ container to the organ perfusion apparatus during perfusion of the organ or tissue locatable in the basin; and
- a coarse filter covering the opening at the bottom of the basin so as to be configured to filter any of the perfusate that flows through the opening by preventing large particles in the perfusate from entering the opening, while ensuring a sufficient flow rate of the perfusate through the opening to maintain the perfusion of the organ or tissue, wherein:
- the coarse filter is located so that, during the perfusion of the organ or tissue, the coarse filter is accessible to a practitioner by way of another opening in the organ container, and
- the filtering apparatus is configured so that, in use, (i) the perfusate flows downward through the coarse filter and (ii) the perfusate flows downward from the coarse filter through the opening so as to exit the organ container.

* * * * *